(12) United States Patent
Hunter

(10) Patent No.: US 9,913,737 B2
(45) Date of Patent: Mar. 13, 2018

(54) MECHANICAL FINGER

(71) Applicant: Mark Hunter, Marina del Rey, CA (US)

(72) Inventor: Mark Hunter, Marina del Rey, CA (US)

( * ) Notice: Subject to any disclaimer, the term of this patent is extended or adjusted under 35 U.S.C. 154(b) by 0 days.

(21) Appl. No.: 14/207,635

(22) Filed: Mar. 13, 2014

(65) Prior Publication Data

US 2016/0235555 A1 Aug. 18, 2016
US 2017/0014245 A9 Jan. 19, 2017

Related U.S. Application Data

(60) Provisional application No. 61/780,622, filed on Mar. 13, 2013.

(51) Int. Cl.
*A61F 2/50* (2006.01)
*A61F 2/58* (2006.01)
*A61F 2/68* (2006.01)
*A61F 2/70* (2006.01)
*A61F 2/76* (2006.01)

(52) U.S. Cl.
CPC ...... *A61F 2/586* (2013.01); *A61F 2002/5009* (2013.01); *A61F 2002/5072* (2013.01);
(Continued)

(58) Field of Classification Search
CPC .. A61F 2/54; A61F 2/583; A61F 2/586; A61F 2/588; A61F 2002/543;
(Continued)

(56) References Cited

U.S. PATENT DOCUMENTS 2,568,298 A * 9/1951 Philpott ................. A61F 2/586
623/64
5,888,246 A 3/1999 Gow
(Continued)

FOREIGN PATENT DOCUMENTS

WO WO 2008092695 A1 * 8/2008 ............... A61F 2/58
WO WO 2012039479 A1 * 3/2012

OTHER PUBLICATIONS

Derwent abstract of WO2011001136. Published Jan. 6, 2011. (US document 20130053984 used as certified translation).*

*Primary Examiner* — Thomas J Sweet
*Assistant Examiner* — Christie Bahena
(74) *Attorney, Agent, or Firm* — Schlee IP International, P.C.; Alexander R. Schlee

(57) ABSTRACT

The invention relates to a mechanical finger comprising, a knuckle, a proximal element, a rod, a motor, a motor driven screw and a distal element. The knuckle has a first and second pivot. The proximal element knuckle end is coupled to the first pivot. The proximal element also has a third pivot at a variable longitudinal distance from the first pivot. The rod has a near end pivotally coupled to the second pivot and a far end pivotally coupled to the third pivot. A motor is coupled to and referenced to the proximal element. A screw is driven to change the distance between the third pivot and the first pivot in response to a command from a controller to the motor. A distal element is pivotally coupled to the proximal element. The distal element rotates with respect to the proximal element in response to a change in the variable distance between the third pivot and the first pivot.

4 Claims, 20 Drawing Sheets

(52) U.S. Cl.
CPC . *A61F 2002/6845* (2013.01); *A61F 2002/701* (2013.01); *A61F 2002/762* (2013.01)

(58) Field of Classification Search
CPC .......... A61F 2002/546; A61F 2002/587; A61F 2002/762; B25J 15/0006; B25J 15/0009; B25J 15/0015; B25J 15/0021; B25J 15/08; B25J 15/123
USPC .......................... 623/24, 25, 57, 58, 63, 64
See application file for complete search history.

(56) References Cited

U.S. PATENT DOCUMENTS

| | | |
|---|---|---|
| 6,908,489 B2 | 6/2005 | Didrick |
| 8,100,986 B2 | 1/2012 | Puchhammer et al. |
| 8,491,666 B2 | 7/2013 | Schulz |
| 8,747,486 B2 * | 6/2014 | Kawasaki et al. ............... 623/64 |
| 2006/0224249 A1 * | 10/2006 | Winfrey .................. A61F 2/583 623/64 |
| 2008/0127768 A1 | 6/2008 | Shirai et al. |
| 2008/0215162 A1 * | 9/2008 | Farnsworth et al. ........... 623/57 |
| 2012/0146352 A1 * | 6/2012 | Haslinger ................ A61F 2/586 294/198 |
| 2012/0169081 A1 | 7/2012 | Takenaka et al. |
| 2013/0053984 A1 * | 2/2013 | Hunter et al. ................... 623/64 |
| 2013/0104686 A1 | 5/2013 | Yamazaki |
| 2013/0226315 A1 | 8/2013 | Varley |
| 2013/0331949 A1 | 12/2013 | Dehoff et al. |
| 2014/0107805 A1 | 4/2014 | Varley |

* cited by examiner

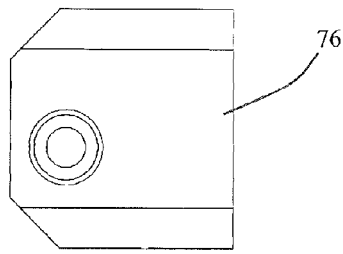
Fig 11a
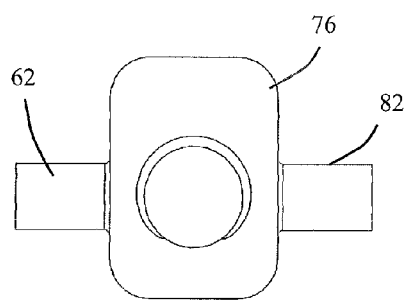
Fig 11b
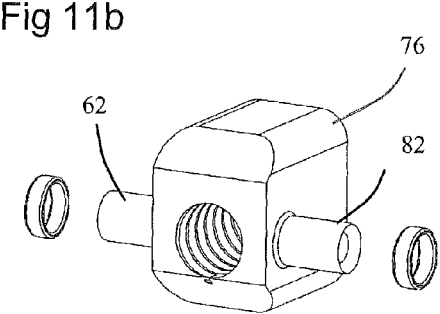
Fig 11c
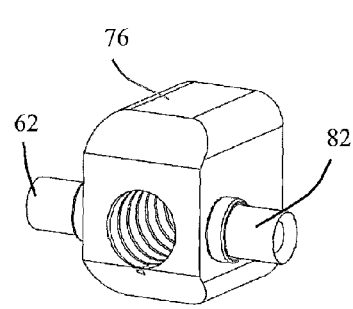
Fig 11d
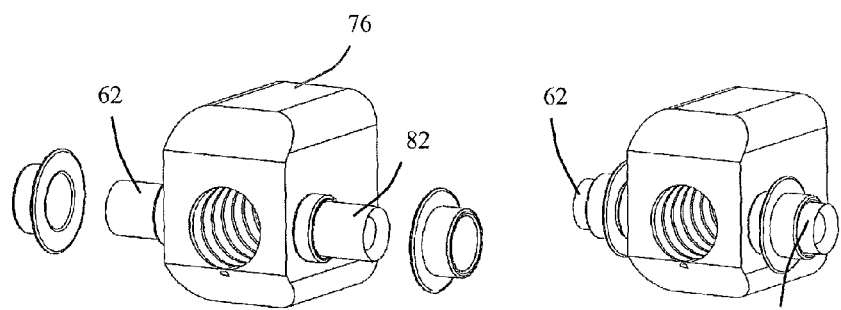
Fig 11e
Fig 11f

MECHANICAL FINGER

This invention claims priority from provisional patent application Ser. 61/780,622 filed 13 Mar. 2013 for a Prosthetic Finger Design having a common sole inventor.

STATEMENT REGARDING FEDERALLY SPONSORED RESEARCH OR DEVELOPMENT

This invention was not developed with Government funded effort.

FIELD OF THE INVENTION

This invention relates to the field of prosthetic appliances made for and used by human amputees and more particularly to those amputees that have lost one or more fingers on a hand.

BACKGROUND OF THE INVENTION

U.S. Pat. No. 8,100,986 issued on Jan. 24, 2012 to inventor Gregor Puchhammer of Vienna (AT) shows a mechanical prosthetic finger with a proximal member, a medial member and a distal member all mounted pivotally on one another. A moveable balance arm is connected via leavers to the proximal member and to the distal member. However the Puchhammer '986' reference does not show the simpler arrangement of a screw nut assembly in a proximal element cavity having a left and right pivot boss extending through the left and right slots in the proximal element cavity. The left and right pivot boss are each sized to provide free longitudinal movement within its respective left guide and right slots so as to prevent the screw nut assembly from rotating in the proximal element cavity as the screw nut assembly is moved longitudinally in the proximal element cavity by an axial screw drive.

U.S. Pat. No. 5,888,246 issued Mar. 30, 1999 to inventor David J. Gow of Edinburgh (GB) from application Ser. No. 08/702,605 filed Mar. 10, 1995. The '246' patent is related art but it fails to show a screw nut assembly in a proximal element cavity having a left guide and pivot boss extending through the left slot and a right guide and pivot boss extending through the right slot of the proximal element cavity. The left and right pivot boss are each sized to provide free longitudinal movement of the left and right boss toward the distal element or toward the knuckle end of the proximal element within its respective left guide or right guide while preventing the screw nut assembly from rotating in the proximal element cavity as the screw nut assembly is moved longitudinally in the proximal element cavity by a direct longitudinal screw drive.

Mechanical fingers for artificial hands require various features to best perform the functions for an upper limb prosthetic user. The required features and functions include a high strength force generator, a light weight, good reliability, adequate speed, and a size that permits a cover that provides a natural appearance. These features are made difficult to include by the small space available inside an individual finger.

Another feature that is difficult to achieve in the design of a prosthetic mechanical finger is the short section where the prosthetic finger attaches to the residual end of the finger on the patient. Previous embodiments have placed the force generators or a part of the drive mechanism inside the build height which extends the length of the prosthetic to a position that is outside of the natural envelope of a finger. A longer than natural build height tends to result in fewer patients being fitted with a prosthetic finger. The shorter build height made possible by the invention is expected to improve the market acceptance of the prosthetic with expanded sales including sales to females and teenagers.

Another feature made possible by the invention prosthetic is a reduced cost flowing from its reduced complexity. Earlier embodiments have higher part counts with parts of significant complexity that contributed to a higher price for the prosthetic.

SUMMARY OF THE INVENTION

It is an object of the present invention to solve or reduce many of the problems stated above. The mechanical finger as taught by this disclosure, in a first embodiment that comprises the following components as referenced in FIGS. 1a-1c: a knuckle (12), a proximal element (24), a rod (18), a screw nut boss (22), a force generator (26) with an axial drive shaft driving a screw that is axially coupled to the screw nut assembly, and a frame (10) means for coupling the knuckle (12) to the stump or residual limb of the patient. The knuckle (12) is coupled to the frame (10) and has a first (14) and second pivot (16) separated by a first predetermined distance. The proximal element has a knuckle end and a distal end. The knuckle end of the proximal element is coupled to the first pivot (14). The proximal element provides a third pivot (21). The third pivot is located on the proximal element (24) at a variable longitudinal distance from the first pivot (14).

It should be understood that the each of the three pivots characterized herein, and later a fourth pivot, are characterized in the structure of the invention mechanical finger by a corresponding left and right counterpart, each left and right counterpart being axially aligned, the axis of each pivot being normal to a plane that contains the longitudinal axis of the axial screw drive to the screw nut assembly.

The rod (18) having a near end pivotally coupled to the second pivot (16) and a far end of the rod (18) is pivotally coupled to the third pivot (21). A screw (74) drives the screw nut boss (22). The force generator (26) is coupled to or referenced to the proximal element (24), and more particularly to the near end or knuckle end of the proximal element cavity. The screw (74) is coupled to the third pivot (21) to change the variable longitudinal distance between the third pivot (21) and the first pivot (14) in response to a command from a controller to the force generator (26).

A distal element (38) is pivotally coupled to the proximal element at a fourth pivot (36). The distal element (38) rotates with respect to the proximal element (24) in response to a change in the variable distance between the third pivot (21) and the first pivot (14). The distal element (38) further has at least a first phalange pivotally coupled to the fourth pivot (36) on the proximal element (24). Each phalange has a distal element slot (47) characterized to receive a screw nut boss (22) through a proximal element slot (42) then passing through the distal element slot (47).

Movement of the screw nut boss (22) toward the knuckle (12) results in a counter clockwise torque applied to the distal element (38) around the fourth pivot (36) as the screw nut boss (22) engages the wall of the distal element slot (47). Movement of the screw nut boss (22) toward the distal end of the proximal element (24) results in a clockwise torque applied to the distal element (38) around the fourth pivot (36) as the screw nut boss (22) engages the wall of the distal element slot (47). In another alternative embodiment, the mechanical finger comprises a frame coupled to the knuckle and formed to receive and be attached to the residual limb of a patient. The mechanical finger also has an elastic or spring element (46) extending in tension from the distal element (38) to the proximal element (24) to add to the grip force of the finger as it closes and to help to maintain a limited closed grip on the object grasped as the power to the force generator is interrupted.

The screw nut assembly within the proximal element cavity has a left guide and pivot boss extending through a left slot and a right guide and pivot boss extending through a right slot, each guide and pivot boss extending through its respective slot. As explained above, the force generator or motor rotates the screw that is engaged with the screw nut assembly. The screw nut assembly carries the left and right pivot boss in its slot, each pivot boss being sized to provide free longitudinal movement within its respective left guide and right guide to prevent the screw nut assembly from rotating in the proximal element cavity. The rotation of the screw is transferred into a linear movement of the third pivot as the screw nut assembly is moved longitudinally through the proximal element cavity.

BRIEF DESCRIPTION OF THE DRAWINGS

An example of a mechanical finger embodying the present invention will now be described in greater detail with reference to the accompanying drawings, in which;

FIG. 11a shows a side view of the screw nut, FIG. 11b shows a front view of the screw nut, FIG. 11c shows a perspective view of the screw nut with x2 washers, FIG. 11d shows a perspective view of the screw nut with x2 washers, FIG. 11e shows a perspective view of the screw nut with x4 washers fitted, FIG. 11f shows a perspective view of the screw nut with x4 washers fitted.

DESCRIPTION OF THE INVENTION

Figure 1A:
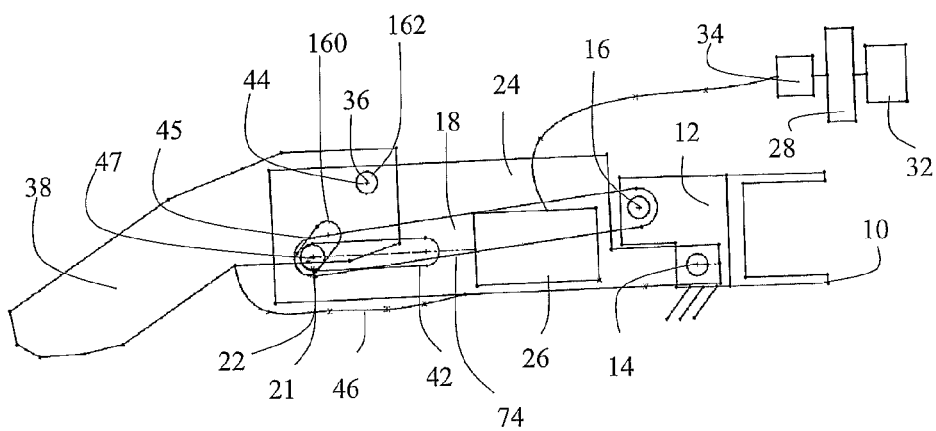
FIG. 1a shows a schematic stick drawing of the mechanical finger in the fully open position.

The invention Mechanical Finger will now be discussed with reference to FIG. 1 through FIG. 16b with FIG. 1a being a simplified stick drawing showing frame 10 which attaches to the amputee residual limb, and the knuckle 12 attached to the frame 10. The knuckle 12 has a first pivot 14 and a second pivot 16. The knuckle end of the rod 18 is attached to the knuckle 12 at the second pivot 16. The distal end of the rod 18 is attached to the rod to screw nut boss 22. The proximal element 24 contains the force generator 26 that is connected to and can push and pull the screw nut boss 22 in a longitudinal direction. The force generator 26 is powered by the battery 28, and controlled by the control sensor 32 and the processor 34. The proximal element 24 has a fourth pivot 36 which connects the proximal element 24 to the distal element 38. The proximal element 24 has a proximal element slot 42 that guides the screw nut boss 22 in a longitudinal direction. The distal element 38 has a distal element slot 47 which contains the screw nut boss 22. As the force generator actuates the screw nut boss 22, the distal element slot 47 accommodates the linear movement of the screw nut boss 22 as it travels through the arc from the fourth pivot 36 and pulls the distal element 38 closed. The elastic or spring element 46 is connected to the distal element 38 and the proximal element 24 to maintain force when the power is interrupted.

Figure 1B:
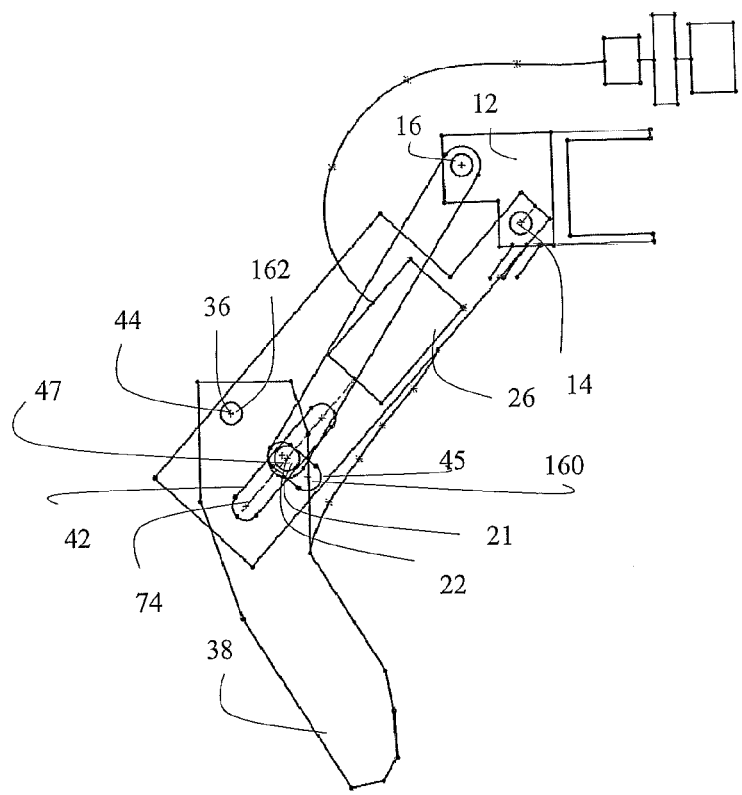
FIG. 1b shows a schematic stick drawing of the mechanical finger in a partially flexed position.

FIG. 1*b* being a simplified stick drawing showing the force generator 26 as it has pulled the screw nut boss 22 towards the knuckle 12 to a part closed position of the mechanical finger. The screw nut boss 22 travels through the proximal element slot 42, as it does the distance between the screw nut boss 22 and the first pivot 14 gets shorter, because the screw nut boss 22 and the second pivot 16 are always the same distance apart due to the length of the rod 18, the first pivot 14 is actuated towards a closed position. The screw nut boss 22 is connected to the distal element slot 47. As the screw nut boss 22 is pulled towards the knuckle 12 the distal element slot 47 is rotated around the fourth pivot 36.

Figure 1C:
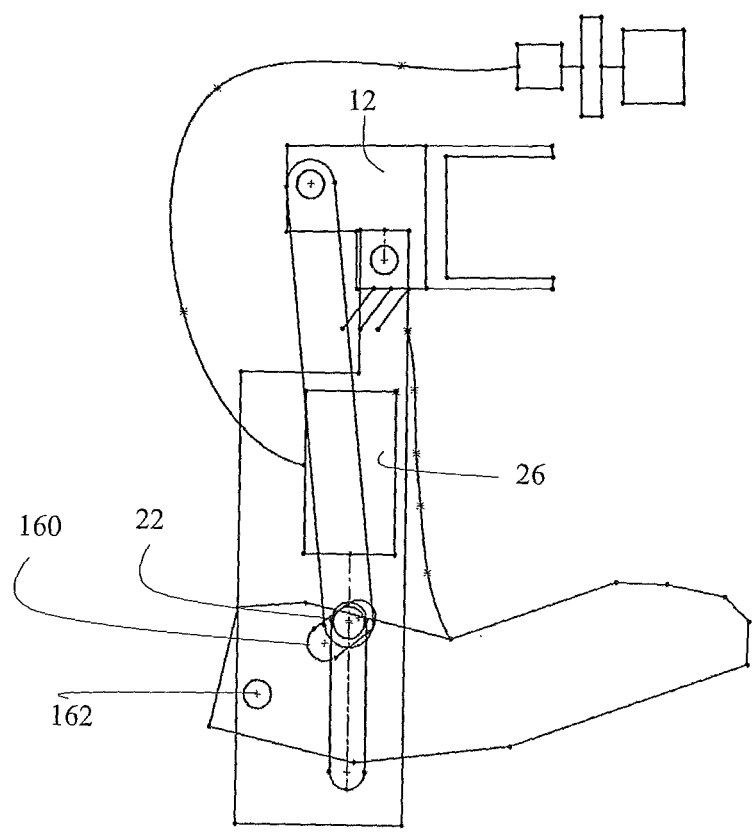
FIG. 1c shows a schematic stick drawing of the mechanical finger in a fully flexed position.

FIG. 1*c* is another schematic simplified stick drawing showing the force generator 26 as it has pulled the screw nut boss 22 towards the knuckle 12 to a fully closed position of the finger.

Figure 2A:
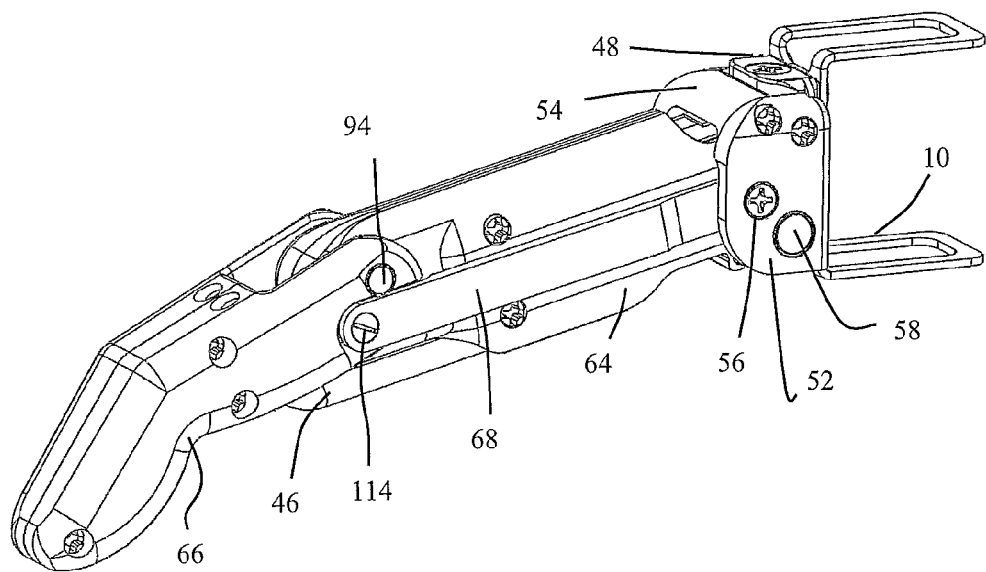
FIG. 2a is a perspective view of the mechanical finger shown in the fully open position.

FIG. 2*a* is a perspective view of the mechanical finger assembly shown if greater detail than FIG. 1 in the fully open position. The frame 10 is connected to the knuckle to frame mount 48 which connects the left knuckle 52 and the right knuckle 54 to the frame 10. The left knuckle 52 contains the left second pivot 56 and the left first pivot 58. The left rod 68 is shown coupled to and extending from the left rod to third pivot 114 to the left second pivot 56. The left proximal element 64 is connected to the left knuckle 52 at left first pivot 58. The left proximal element 64 is connected to the left distal element 66 at the left fourth pivot 94. The elastic or spring element 46 is connected in tension to the left distal element 66 and the left proximal element 64.

Figure 2B:
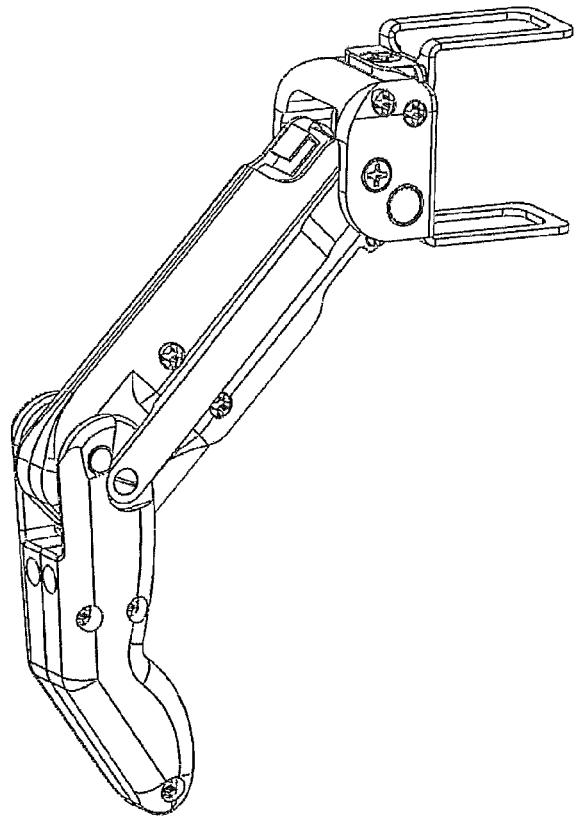
FIG. 2b is a perspective view of the mechanical finger shown in a partially flexed position.

FIG. 2*b* is a perspective view of the mechanical finger assembly shown in the partially closed position.

Figure 2C:
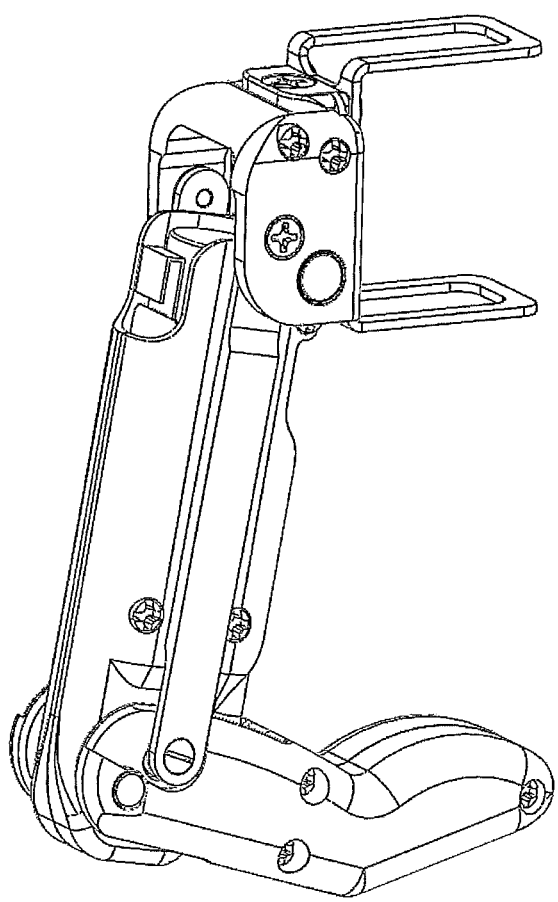
FIG. 2c is a perspective view of the mechanical finger shown in fully flexed position.

FIG. 2*c* is a perspective view of the mechanical finger assembly shown in the fully closed position.

Figure 3A:
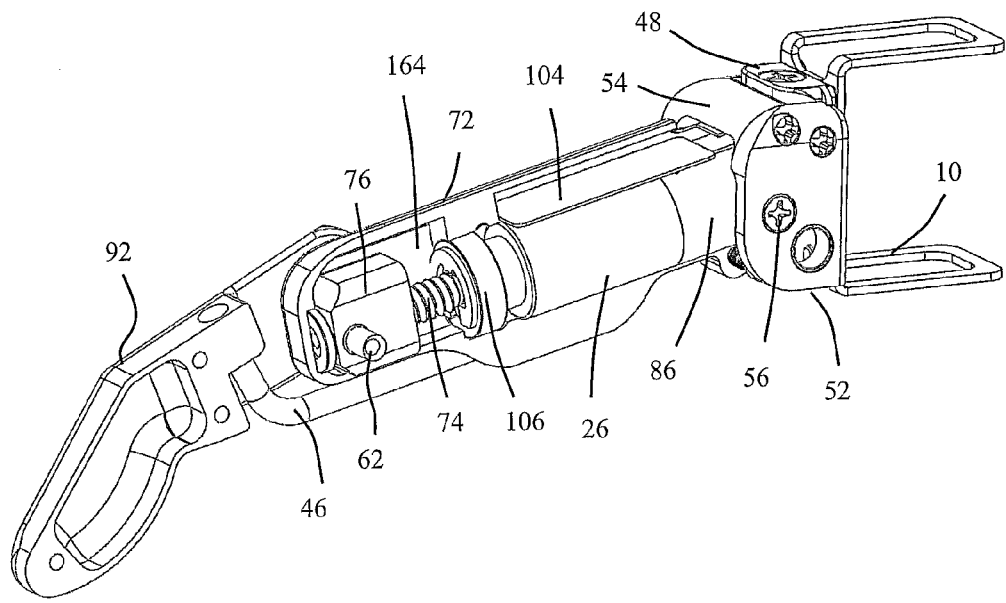
FIG. 3a shows a partial sectional perspective view of the mechanical finger in the fully open position, showing the drive mechanism.

FIG. 3*a* shows a partial sectional view of the mechanical finger. The left proximal element 64, the left distal element 66 and the left rod 68 have been removed for clarity. Inside the left proximal element 64 and the right proximal element 72 is the force generator 26 which is connected to the screw 74. When the force generator 26 receives a drive command it rotates to move the screw 74 in a clockwise or counter clockwise direction. The screw nut 76 is threaded onto the screw 74. The screw nut 76 has a left third pivot 62 which extends through the left proximal element slot 78 (not shown). Although the left proximal element slot 78 is not shown on FIG. 3*a*, 3*b* or 3*c*, that feature can be seen on FIGS. 13*a*, 13*b* and 13*c*. The right third pivot 82 (not shown) extends though the right proximal element slot 84 (not shown). As the left and right pivot bosses extend through the respective left and right proximal element slots, they serve to prevent the screw nut 76 from rotating inside the proximal element cavity in response to rotation of the screw 74 as the prosthesis is commanded to operate. Rotation of screw 74 in the screw nut 76 exerts a torsional force on the screw nut 76. By preventing the screw nut 76 from rotating, the torque applied to the screw nut 76 is converted and combined with the inclined plane of the screw thread to provide an axial linear force to the third pivot 21 (shown in FIGS. 1*a*-*c*) via the left and right boss as they extend through the left proximal element slot 78 (not show) and right proximal element slot 84 (not shown).

Figure 3B:
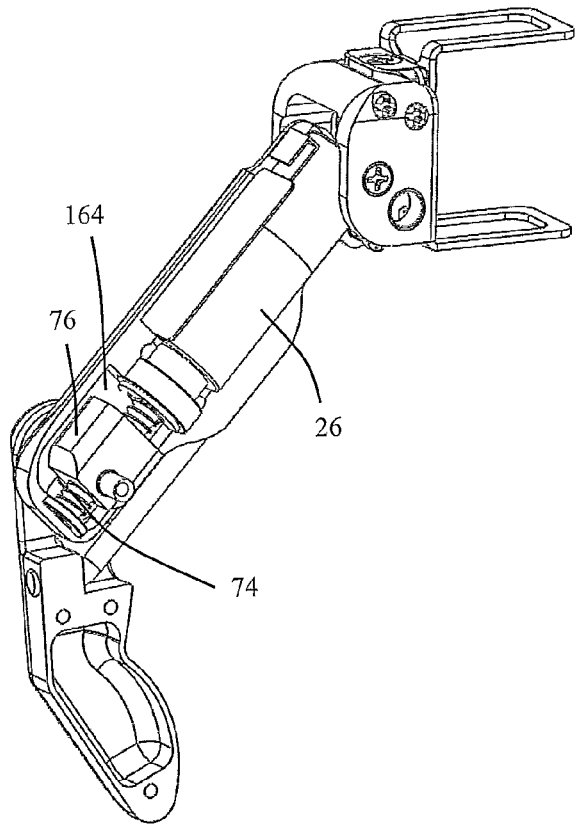
FIG. 3b shows a partial sectional perspective view of the mechanical finger in the partially closed position, showing the drive mechanism.
Figure 3C:
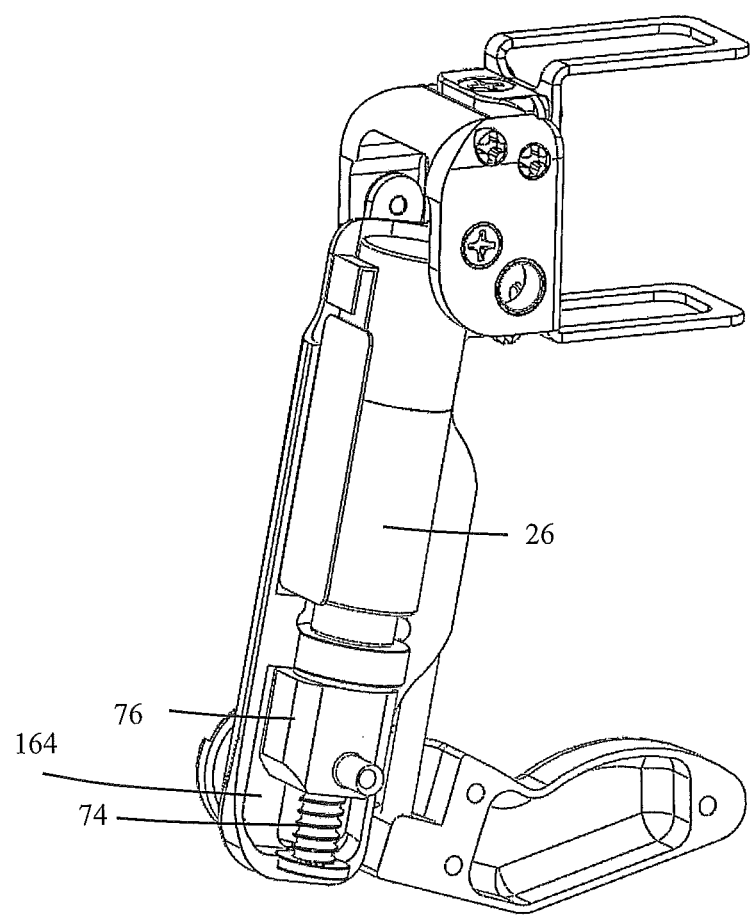
FIG. 3c shows a partial sectional showing the drive mechanism in a perspective view of the mechanical finger in the fully closed position.

FIG. 3*b* shows a partial view of the mechanical finger in the partially closed position with the screw nut 76 being at its middle position on the length of the screw 74. FIG. 3*c* shows a partial sectional view of the mechanical finger in the fully closed position with the screw nut 76 moved to a limit on screw 74 toward the motor or force generator 26.

Figure 4A:
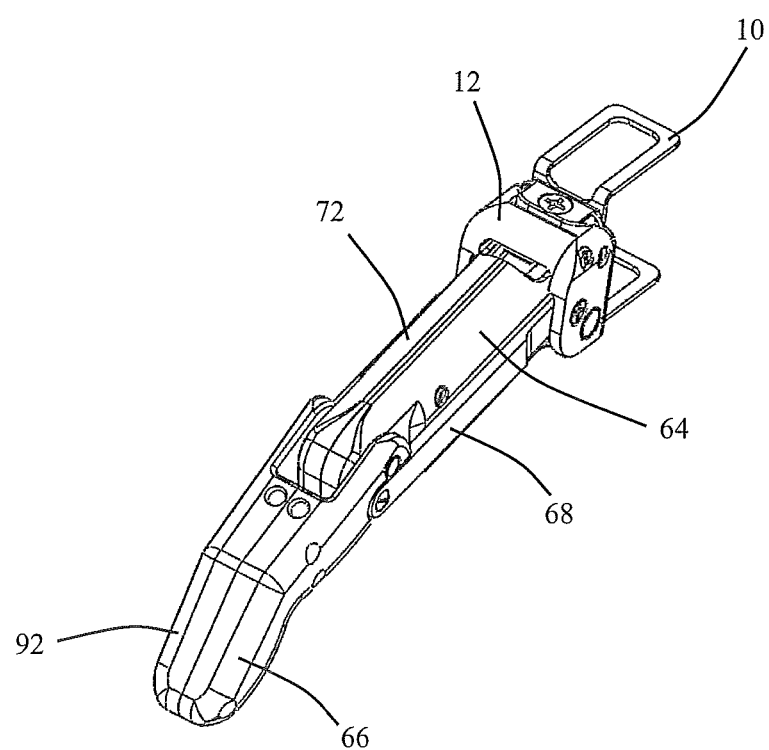
FIG. 4a is a perspective view of the mechanical finger.
Figure 4B:
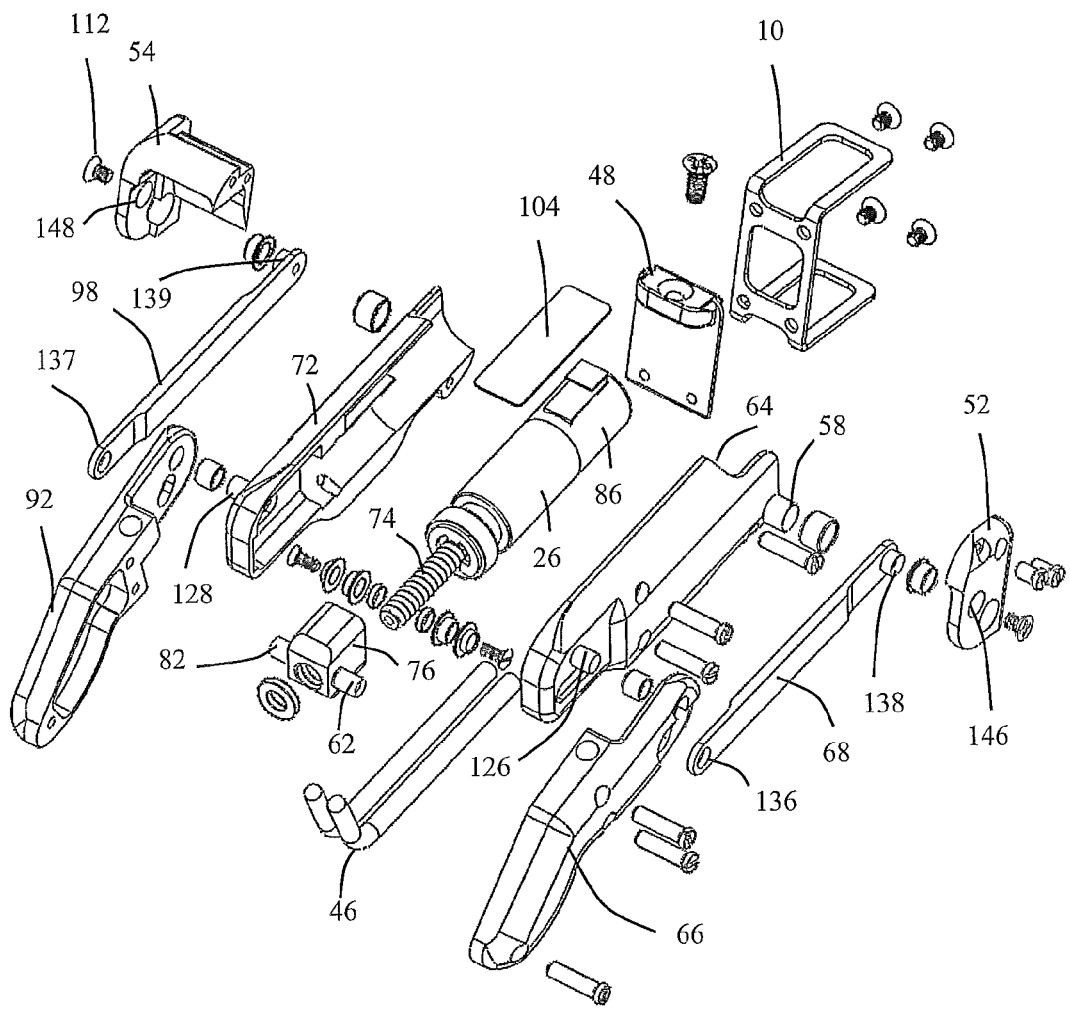
FIG. 4b is a perspective exploded view of FIG. 4a, FIG. 5a shows a plan view of the mechanical finger with a section line A-A.

FIG. 4*a* is a perspective view from above, of the mechanical finger. FIG. 4*b* is an exploded view of FIG. 4*a*. A sensor 86 is positioned in the proximal element cavity between the rear or knuckle end of the motor and the knuckle to frame mount 48. The sensor 86 measures the longitudinal position or distance that the screw nut 76 is at or has traveled along the length of the screw 74 driven by the force generator 26. The force generator 26 is connected to and rotates the screw 74.

As stated earlier, the screw 74 is threaded into the screw nut 76. The screw nut 76 has a left third pivot 62 and a right third pivot 82. These elements constitute the drive mechanism. The drive mechanism is contained inside the proximal element cavity formed by the left proximal element 64 and the right proximal element 72. In operation, as the force generator 26 receives a command or drive signal, the screw 74 turns, the screw nut 76 is prevented from turning by the left proximal element slot 78 and the right proximal element slot 84 shown on FIGS. 8*a* and 8*b*. The slots 78 and 84 allow a linear movement of the screw nut 76 along the threaded length of the screw 74.

With continuing reference to the exploded view of FIG. 4*b*, the left knuckle 52 is connected to the left proximal element 64 at the left first pivot 58. The right knuckle 54 is connected to the right proximal element 72 at the right knuckle to proximal element pivot 88 (not shown). The left knuckle 52 is connected to the right knuckle 54. The knuckle to frame mount 48 is connected to the left knuckle 52 and right knuckle 54. The knuckle to frame mount 48 is connected to the frame 10.

The left distal element 66 is connected to the right distal element 92. The left distal element 66 and right distal element 92 are pivoted on the proximal element at the right fourth pivot 96 (not shown) which is formed by the left fourth pivot boss 126 capturing the left fourth pivot aperture 132 (not shown), and the left fourth pivot 94 (not shown) which is formed by the right fourth pivot boss 128 capturing the right fourth pivot aperture 134 (not shown). The left fourth pivot 94 and the right fourth pivot 96 facilitate the rotational movement of the distal elements 66, 92 relative to the proximal elements 64, 72.

The left rod 68 has a left second pivot boss 138 that captures the left second pivot aperture 146 to form the left second pivot 56. The right rod 98 has rod boss 139 that captures the right second pivot aperture 148 to form the right knuckle to rod pivot 102.

The left rod 68 has a third pivot aperture 136 that is received by the left third pivot 62. The right rod 98 has a right third pivot aperture 137 that receives the right third pivot 82.

Figure 5A:
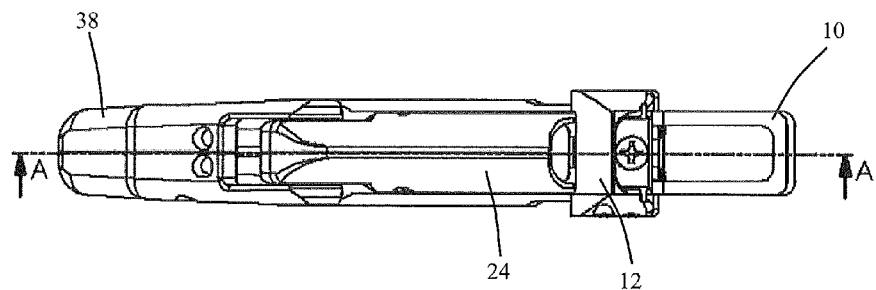
FIG. 5b shows the section view A-A.
Figure 5B:
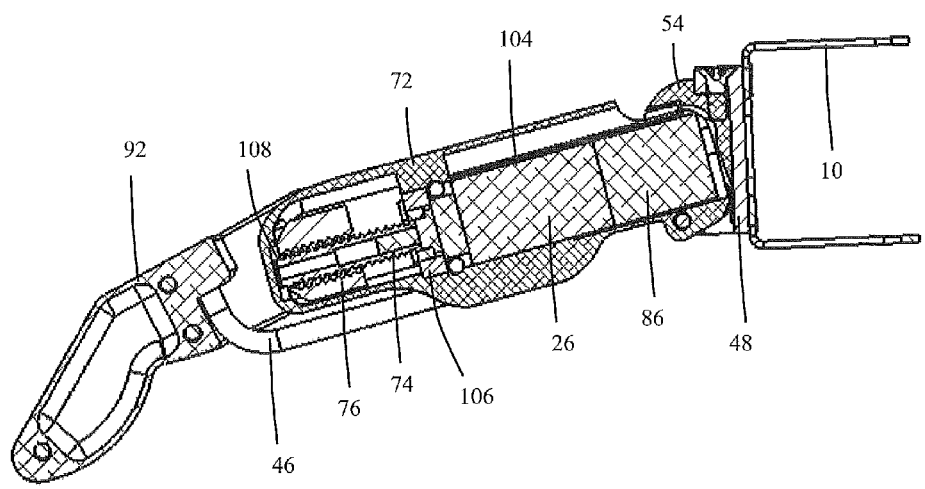

FIG. 5*a* shows a plan view of the mechanical finger with a section line A-A and FIG. 5*b* shows the sectional view of FIG. 5*a* taken on section line A-A. The frame 10 is shown connected to the knuckle to frame mount 48 which is shown connected to the right knuckle 54. The sensor 86 is depicted inside and to the rear of the force generator 26. The microprocessor 104 is shown on top of the force generator 26. The bearing for screw knuckle end 106 and the screw 74 is attached to the left end of the force generator 28. The screw 74 is threaded through the screw nut 76. A bearing for screw distal end 108 is shown that holds the distal end of the screw 74. An elastic or spring element 46 is shown that is joined to the left proximal element 64 (not shown) and right proximal element 72, and to the left distal element 66 (not shown) and right distal element 92. The bearings for screw knuckle end 106 and the bearing for screw distal end 108 protect the screw 74 and the force generator 26 from radial and linear loading.

Figure 6A:
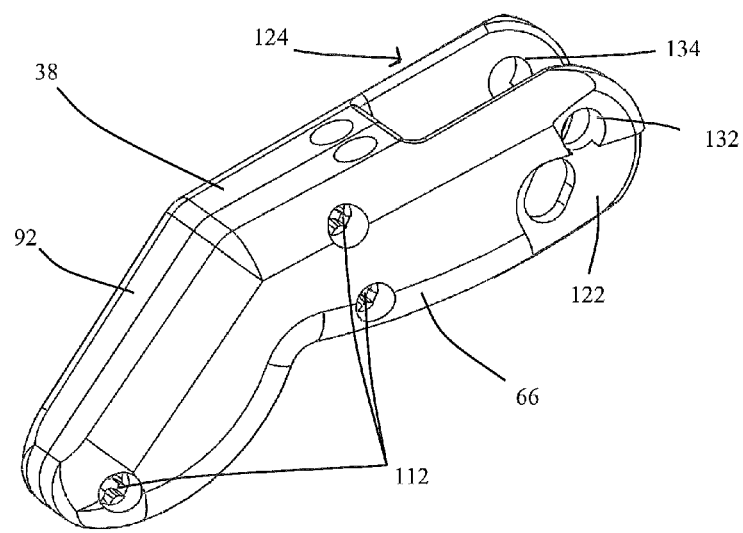
FIG. 6a is a perspective view of the distal element.
Figure 6B:
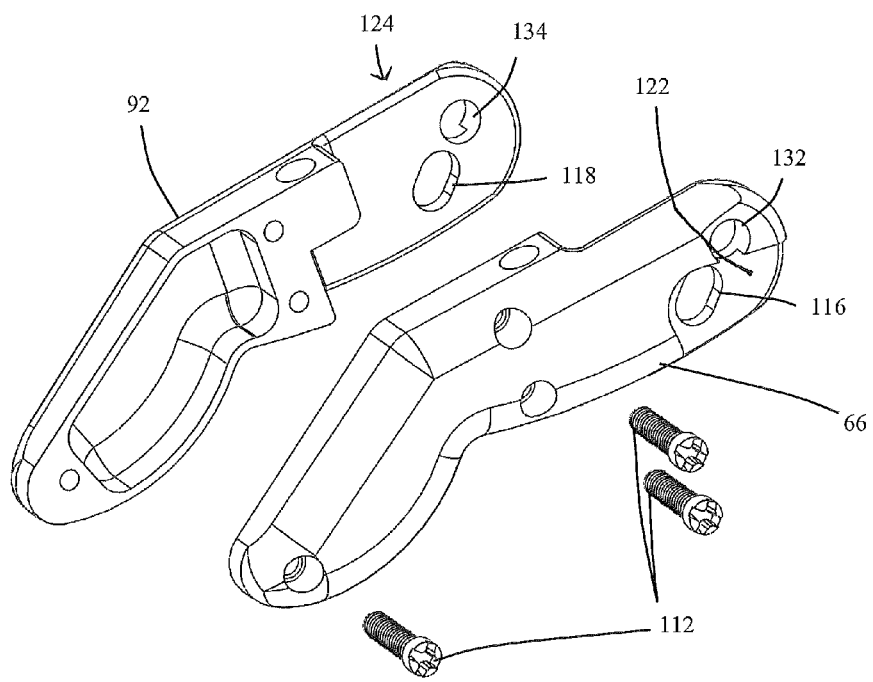
FIG. 6b shows an exploded view FIG. 6a, FIG. 7a is a perspective view of the force generator and the drive mechanism.

FIG. 6*a* shows the left distal element 66 and the right distal element 92 with the assembly screws 112 holding the two in contact with each other to form the distal element 38. The left distal element 66 has a left distal element area 122. The left distal element area 122 has a left fourth pivot aperture 132 and a left distal element slot 116. The right distal element 92 has a right distal element area 124. The right distal element area 124 has a right fourth pivot aperture 134 and a right distal element slot 118. FIG. 6*b* shows an exploded view of FIG. 6*a*. It may be possible to reverse the position and function of the left distal element slot 116 and the right distal element slot 118 with the left fourth pivot aperture 132 and the right fourth pivot aperture 134.

Figure 7A:
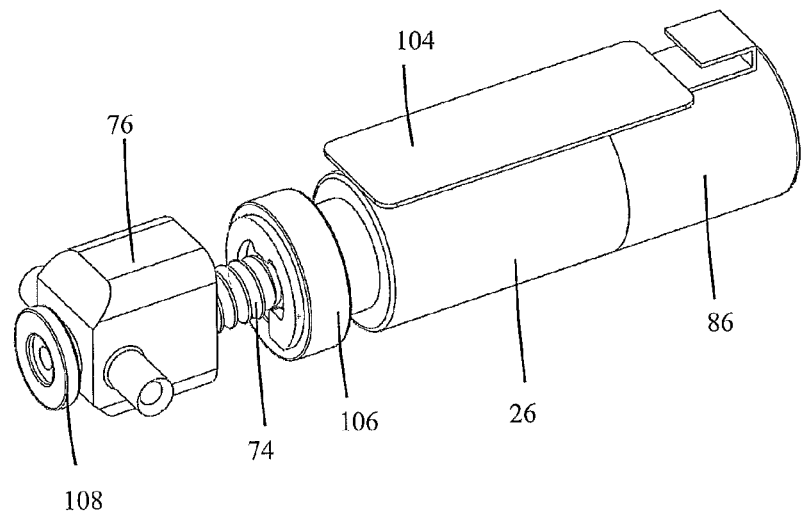
FIG. 7b shows an exploded view of FIG. 7a, FIG. 8a is a perspective view of the proximal element.
Figure 7B:
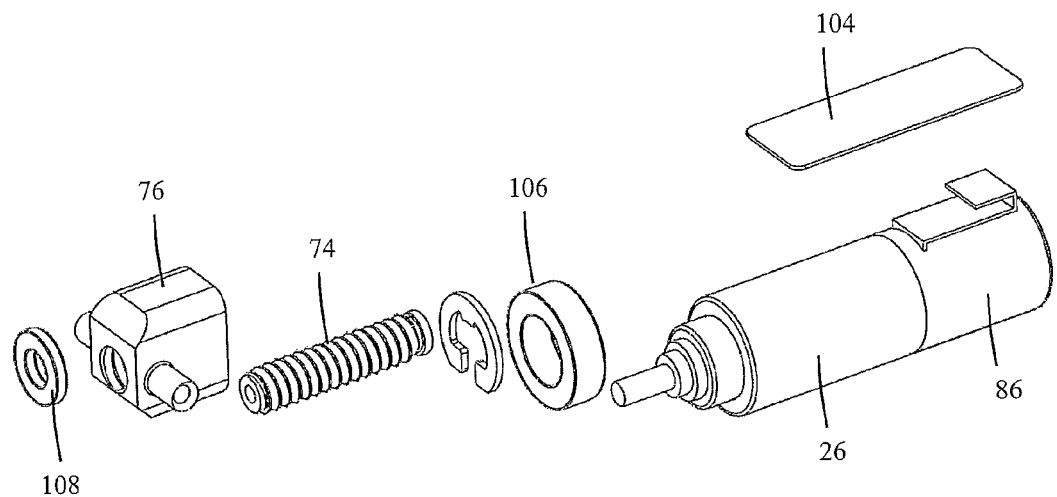

FIG. 7*a* shows the force generator 26 and drive mechanism assembly. The sensor 86 is connected to the force generator 26. The force generator 26 is connected to and drives the screw 74. The screw nut 76 is threaded onto the screw 74. The bearing for screw knuckle end 106 and the bearing for screw distal end 108 are designed to protect the force generator 26 from axial (thrust) and radial loading. FIG. 7*b* is an exploded perspective view of FIG. 7*a*.

Figure 8A:
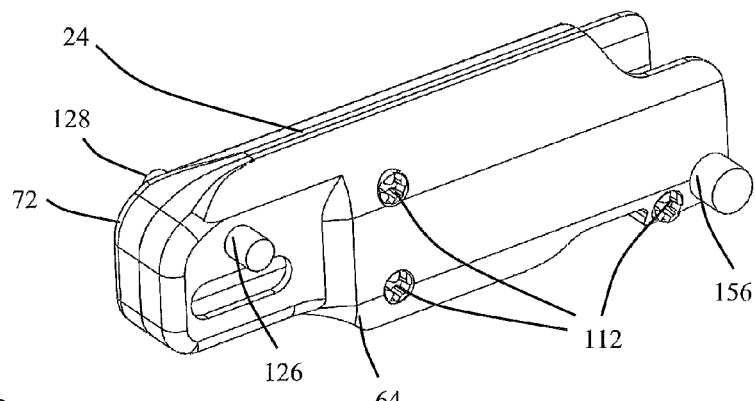
FIG. 8b shows an exploded view of FIG. 8a, FIG. 9a is a perspective view of the knuckle to frame mount and frame mount assembly.
Figure 8B:
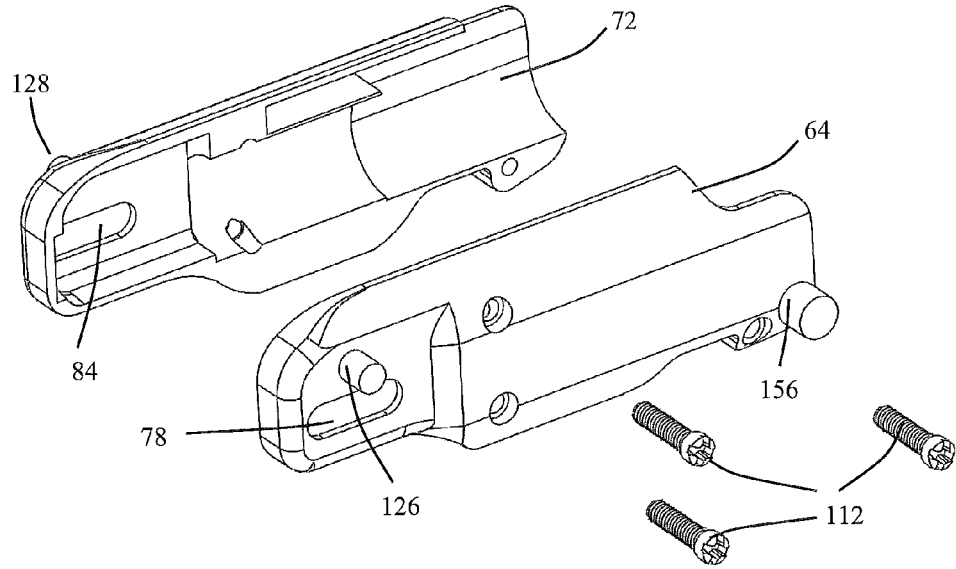

FIG. 8*a* is a perspective view of the assembled proximal formed from a left proximal element 64 and a right proximal element 72. FIG. 8*b* also shows the assembly screws 112 used to couple the left and right sides to form the proximal element 24.

The left fourth pivot boss 126 is shown above the left proximal element slot 78. The right fourth pivot boss 128 is shown above the right proximal element slot 84. The left fourth pivot boss 126 and right fourth pivot boss 128 each respectively extend through the respective left and right fourth pivot apertures 132, 134 on the respective left and right areas 122, 124 of the distal element.

The left fourth pivot boss 126 with the left fourth pivot apertures 132 (shown on FIG. 6.*b*), and the right fourth pivot boss 128 with the right fourth pivot apertures 134 (shown on FIG. 6.*b*), in combination form the fourth pivot 36 (shown on FIG. 1.*a*). The left proximal element 64 has a left first pivot boss 156 that is received by a left first pivot aperture 152 shown on FIGS. 9*a* and 9*b*. The right proximal element 72 has a right first pivot boss 158 (not shown) that is received by a right first pivot aperture 154 also shown on FIGS. 9*a* and 9*b*. The combination of left first pivot boss 156 into the left first pivot aperture 152 and the right first pivot boss 158 into the right first pivot aperture 154 form the first pivot 14. FIG. 8*b* shows an exploded view of FIG. 8*a*.

Figure 9A:
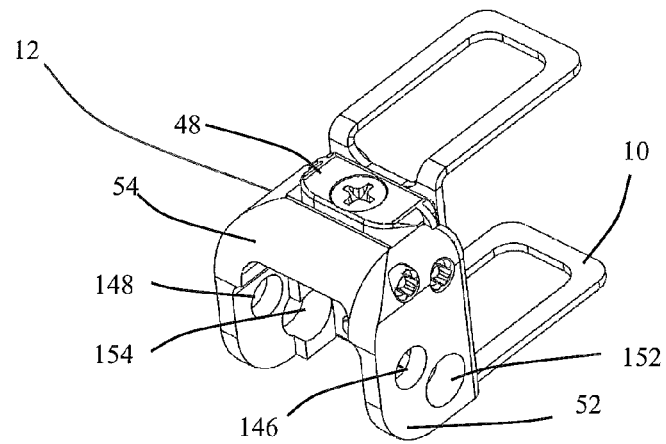
FIG. 9b shows an exploded view of FIG. 9a, FIG. 10a shows a side view of the rod.

FIG. 9*a* is a perspective view of the knuckle 12 formed from a left knuckle 52 and a right knuckle 54 pair of components. The knuckle to frame mount 48 and the frame 10 are also shown. The left knuckle 52 is joined to the right knuckle 54 with two assembly screws 112. The knuckle to frame mount 48 is attached to the left knuckle 52 and right knuckle 54 with screws 112. The frame 10 is attached to the knuckle to frame mount 48 with screws 112. The left knuckle 52 has a left first pivot aperture 152. The right knuckle 54 has a right first pivot aperture 154 as discussed in connection with the above discussion of FIG. 8*a* and FIG. 8*b*.

Figure 9B:
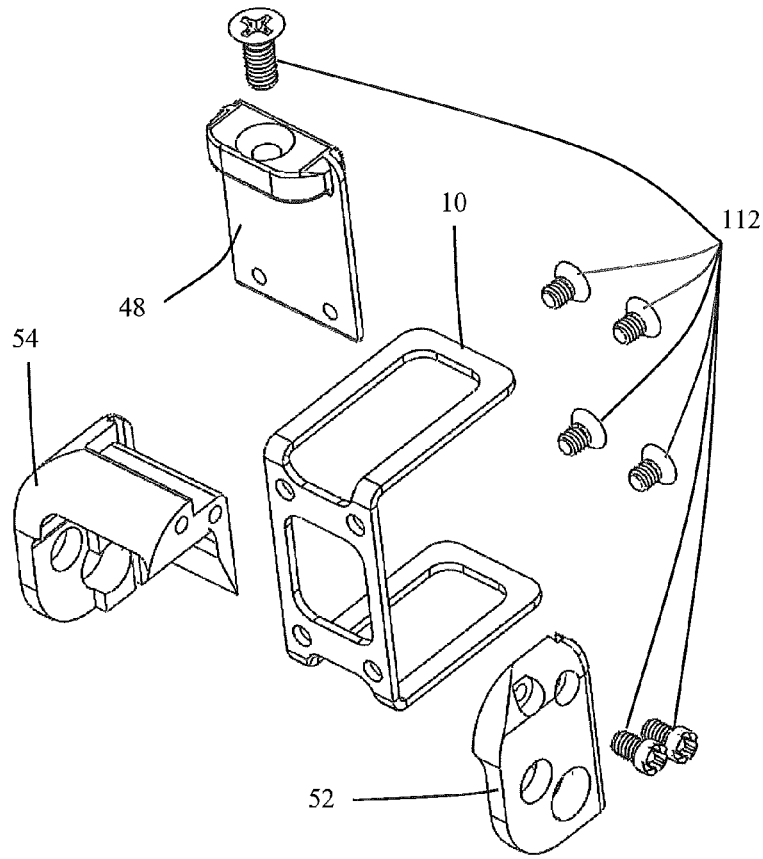
Figure 10A:
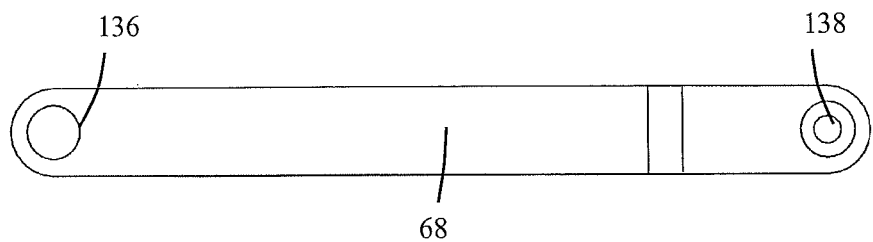
FIG. 10b shows a plan view of the rod.
FIG. 10c shows an exploded view of the rod with bearings.
FIG. 10d shows the rod with bearings fitted.
Figure 10B:
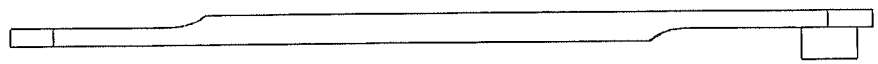
Figure 10C:
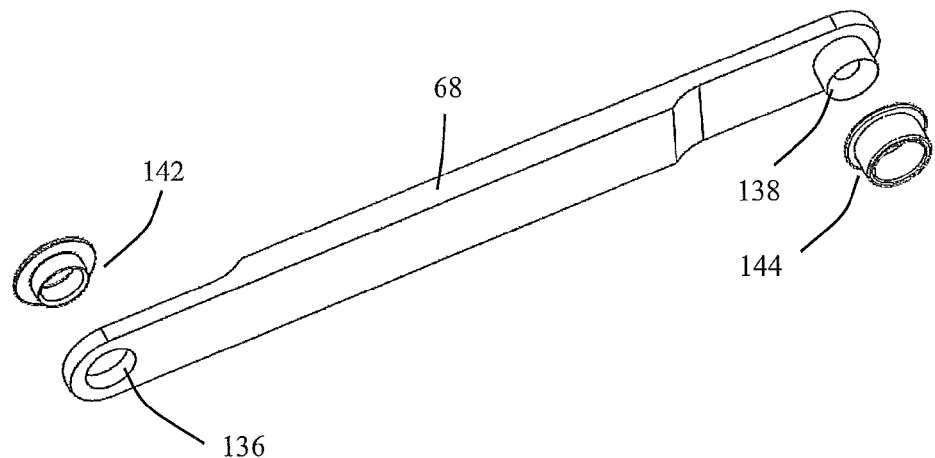
Figure 10D:
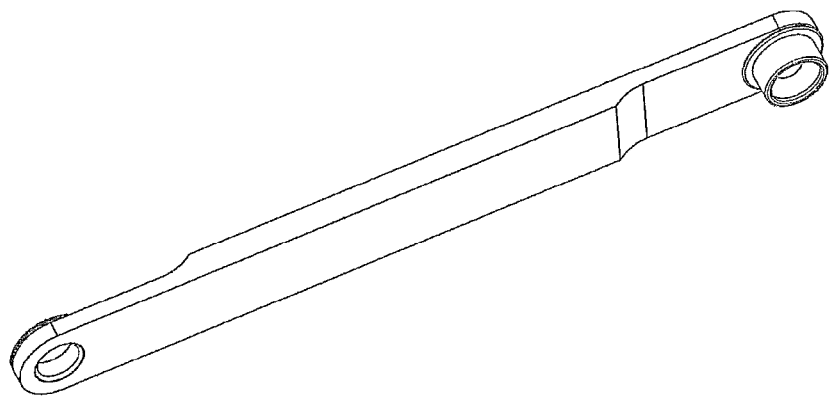

FIG. 9*b* shows an exploded view of 9*a*.

FIGS. 10*a*-10*d* shows the left rod 68. The left rod 68 is the same as the right rod 98 (not shown). The left rod 68 contains a left third pivot aperture 136 that fits onto left third pivot 62 (not shown) to form left rod to third pivot 114. The right rod 98 (not shown) contains a right third pivot aperture 137 that fits onto right third pivot 82 to form right rod to third pivot 120. The combination of the left rod 68 which contains the left third pivot aperture 136 with the left screw nut boss 62 and the right third pivot aperture 137 with the right screw nut boss 82 form the third pivot 21 located on the screw nut boss 22.

The left rod 68 also contains the left second pivot boss 138. The left second pivot boss 138 connects the left rod 68 to the left second pivot 56. To increase efficiency the left rod 68 has a rod aperture bearing 142 inserted into the left third pivot aperture 136, and rod boss bearing 144 inserted onto the left second pivot boss 138. The right rod 98 mirrors the described arrangement of the left rod 68.

The stiffness of the rod contributes to the ability of the mechanical finger to deliver a grip that could exceed design limits. It may be possible to design the rods so as to experience distortion when a design limit is exceeded so as to preclude damage to the structure elements. One possible design embodiment for this purpose could be to design the rods to have a corrugated or curved feature fabricated into the surface of the rod, or to design the rod to have a spring characteristic. The combination of the left second pivot boss 138 with the left second pivot aperture 146 along with the combination of an identical right rod boss 139 (not shown) with the right second pivot aperture 148 form the second pivot 16 shown in FIGS. 1*a*-1*c*.

FIG. 11*a* is a side view of the screw nut 76. FIG. 11*b* is a front view of the screw nut 76. FIG. 11*c* is an exploded view of the screw nut 76 showing the left third pivot 62 and the right third pivot 82 with sleeve bearings ready for installation on the bosses and aligned on each of the bosses.

FIG. 11*d* is a perspective view of the screw nut 76, with sleeve bearings on the left and right screw nut boss. The left third pivot 62 and the right third pivot 82, each with sleeve bearings installed are received by the respective proximal element slots 78, 84 (not shown), and the outer surface of the bearings are sized to ride in the proximal element slots.

FIG. 11*e* is an exploded view of the screw nut 76 with the left third pivot 62 and the right third pivot 82, each being ready to receive a bushing that is stopped by the edge of an earlier sleeve bearing.

FIG. 11*f* is a perspective view showing the screw nut assembly ready for assembly, the bushing on each of the third pivots 62, 82 receiving the respective distal element slot for screw nut boss left and right side 116, 118 (not shown). The sleeves and bearings are added to space the distal element aperture for screw nut boss left and right side from the respective outer surface of the proximal element 24 and add an increase in efficiency between the left third pivot 62 and the right third pivot 82 and the distal element slot left and right side 116, 118.

Figure 12A:
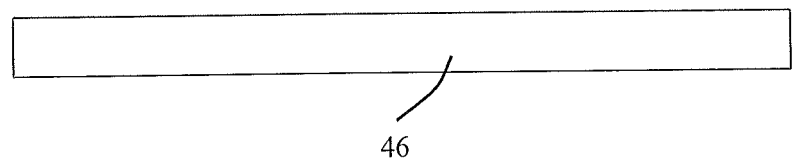
FIG. 12a shows the sprung element side view.
Figure 12B:
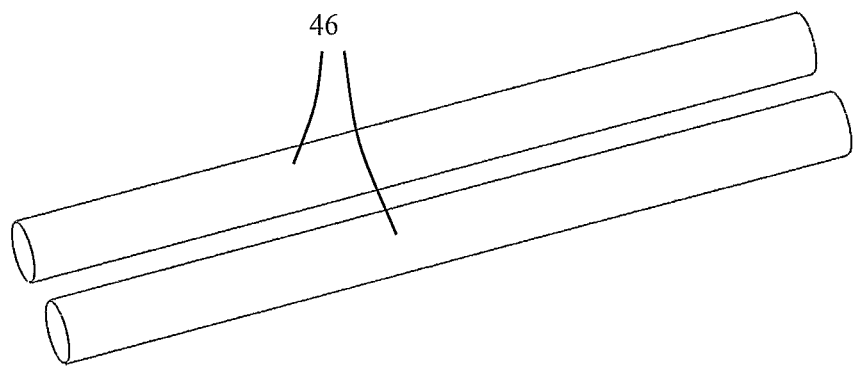
FIG. 12b shows the sprung element in perspective.

FIG. 12*a* is a side view of a single elastic or spring element 46, and FIG. 12*b* is a perspective view of a pair of elastic or spring elements 46.

Figure 13A:
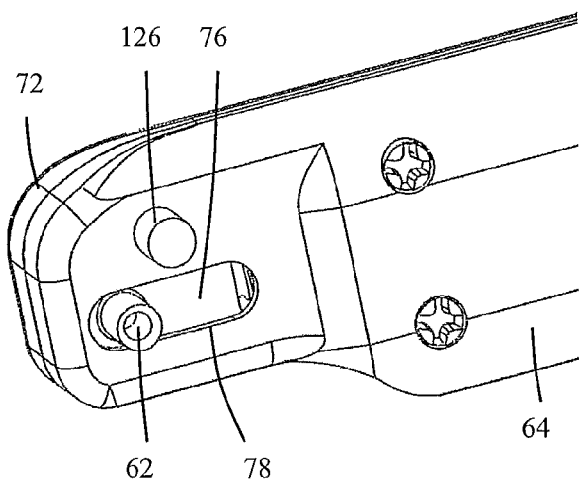
FIG. 13a is a perspective and partial view of the proximal element and screw nut in the fully open position.

FIG. 13*a* is a partial perspective view of the distal end of the left proximal element 64, the right proximal element 72 being partially unseen behind the left side. The left and right sides are assembled together with the screw 74 appearing in FIG. 13*c*. As shown in FIG. 13*a*, as the mechanical finger is fully opened, the left third pivot 62 is at the distal end of the left proximal element slot 78.

Figure 13B:
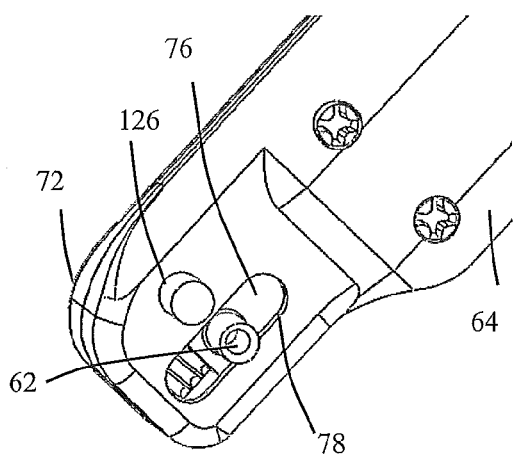
FIG. 13b is a perspective and partial view of the proximal element and screw nut in the partially closed position.

FIG. 13*b* is a partial perspective view of the left proximal element 64 and the right proximal element 72 behind the surface, the two being assembled together with the screw 74 and screw nut 76 in the half way closed position.

Figure 13C:
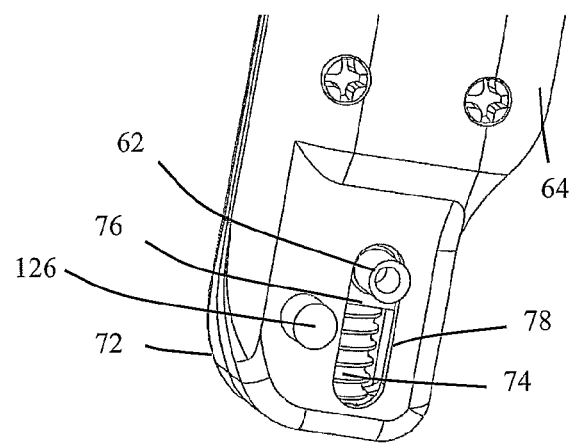
FIG. 13c is a perspective and partial view of the proximal element and screw nut in the fully closed position.

FIG. 13*c* a partial perspective view of the left proximal element 64 and the right proximal element 72 assembled together with the screw 74 and screw nut 76 of the mechanical finger being in the fully closed position.

Figure 14A:
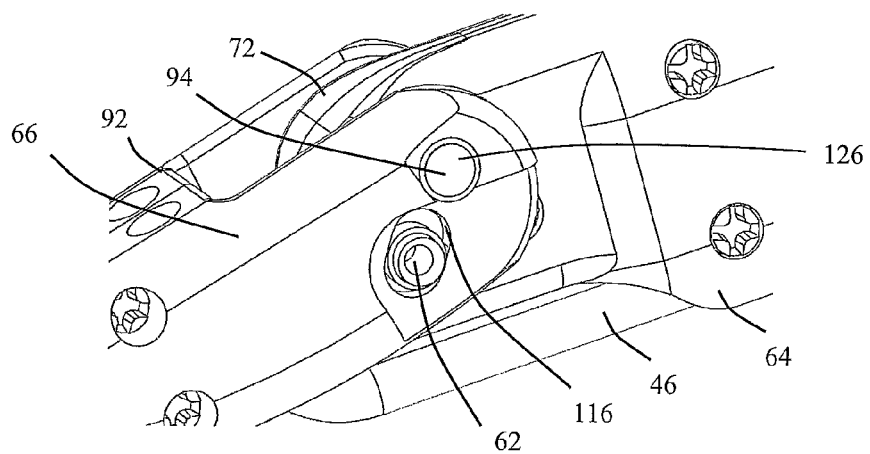
FIG. 14a is a perspective and partial view of the proximal element, screw nut and distal element in the fully open position.

FIG. 14*a* shows a partial view of the proximal element to distal element joint with the finger in a fully opened configuration. The left third pivot 62 is in the lower part of the left distal element slot 116 to the left of the left fourth pivot 94.

Figure 14B:
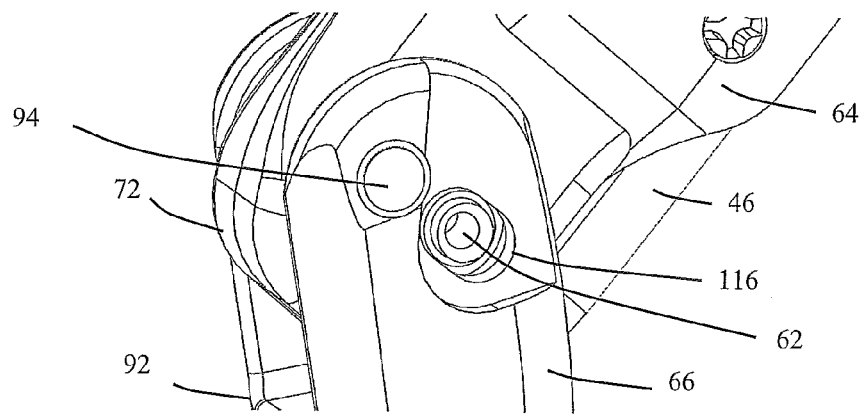
FIG. 14b is a perspective and partial view of the proximal element, screw nut and distal element in the partially closed position.
Figure 14C:
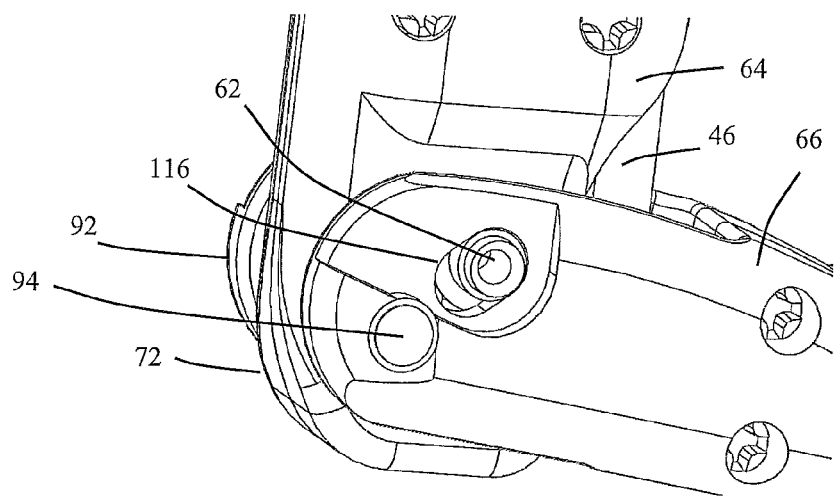
FIG. 14c is a perspective and partial view of the proximal element, screw nut and distal element in the fully closed position.

FIG. 14*b* shows that the left third pivot 62 has moved approximately half way through its actuation travel. The left distal element 66 is pulled by the left third pivot 62 in a counter clockwise rotation towards the knuckle 12. As the left third pivot 62 moves from the position shown in FIG. 14*a*, to FIG. 14*b* and then to FIG. 14*c* within the left proximal element slot 78 (not shown), the left third pivot 62 applies a force to the edge of the left distal element slot 116 that results in a torque applied to the left distal element 66 forcing it to pivot and rotate in a counter clockwise rotation around the left fourth pivot 94. The third pivot 62 touches the inner surface or perimeter of the left distal element slot 116 with a sliding or rolling surface on a fixed slot surface only traversing an arc path along the inner surface of the left distal element slot 116. The arc movement of the left third pivot 62 is accommodated by the left distal element slot 116 as the left third pivot 62 travels upwards in the left distal element slot 116 towards the left fourth pivot 94. In FIG. 14*c* the finger is fully closed; the left third pivot 62 can be seen sitting in the lower part of the left distal element slot 116 away from the left fourth pivot 94.

It will be understood that the right distal element 92 has the same relationship and movement with the right third pivot 82 (not shown) as the left distal element 66 has with the left third pivot 62. FIG. 14*a*-14*c* also shows the elastic or spring element 46 which is attached and connects the left proximal element 64 and the right proximal element 72 to the left distal element 66 and the right distal element 92. The elastic or spring element 46 is in tension, so when the power is interrupted or paused, the elastic or spring element 46 together with the resistance in the force generator 26 and the drive mechanism operate to resist and prevent the mechanical finger from opening. If the mechanical finger is holding an item at the time of the interruption, the item held will remain secured in the grip of the mechanical finger, or fingers as the case may be.

Figure 15A:
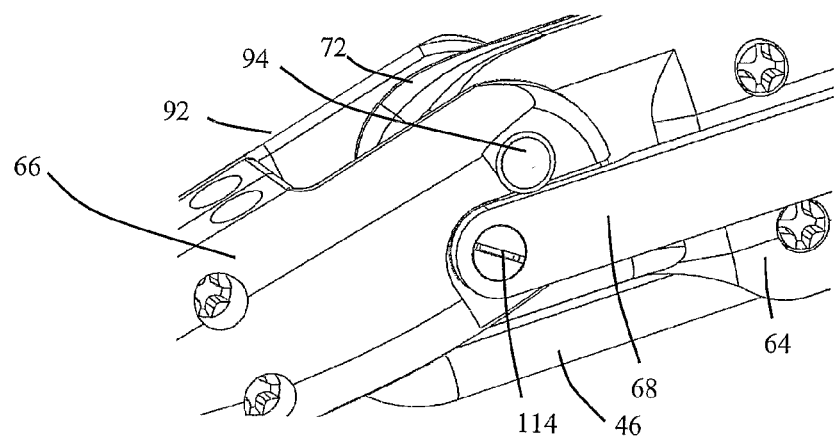
FIG. 15a is a perspective and partial view of the proximal element, rod and distal element in the fully open position.
Figure 15B:
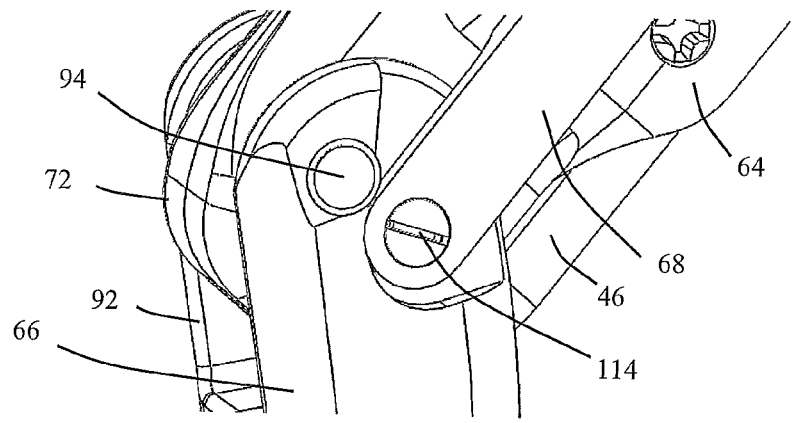
FIG. 15b is a perspective and partial view of the proximal element, rod and distal element in the partially closed position.
Figure 15C:
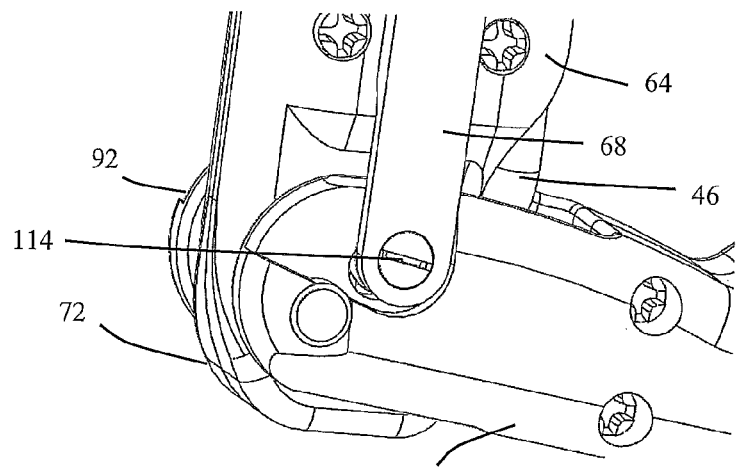
FIG. 15c is a perspective and partial view of the proximal element, rod and distal element in the fully closed position.

FIGS. 15*a*-15*c* are distinguished from FIGS. 14*a*-14*c* by showing the addition of left rod 68 in the FIGS. 15*a*-15*c* series. FIG. 15*a* shows a partial view of the left proximal element 64 and the right proximal element 72 receding into the image. The left proximal element 64 is assembled together with the left rod 68. The left rod 68 is connected to the left third pivot 62 (not shown) at the left rod to third pivot 114. FIG. 15*a* shows the mechanical finger in a fully open position. 15*b* shows the mechanical finger in a partially closed position and FIG. 15*c* shows the mechanical finger in a fully closed position.

Figure 16A:
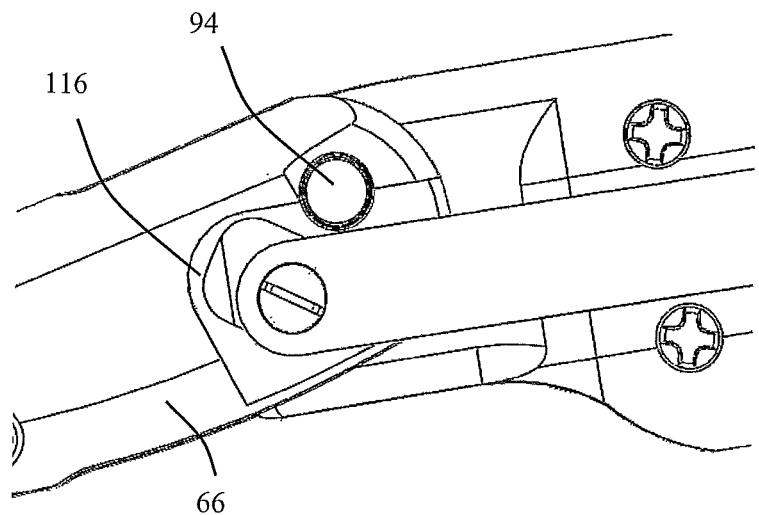
FIG. 16a shows a partial view of the proximal element, rod and distal element in the fully open position, the distal element having an alternative slot design.
Figure 16B:
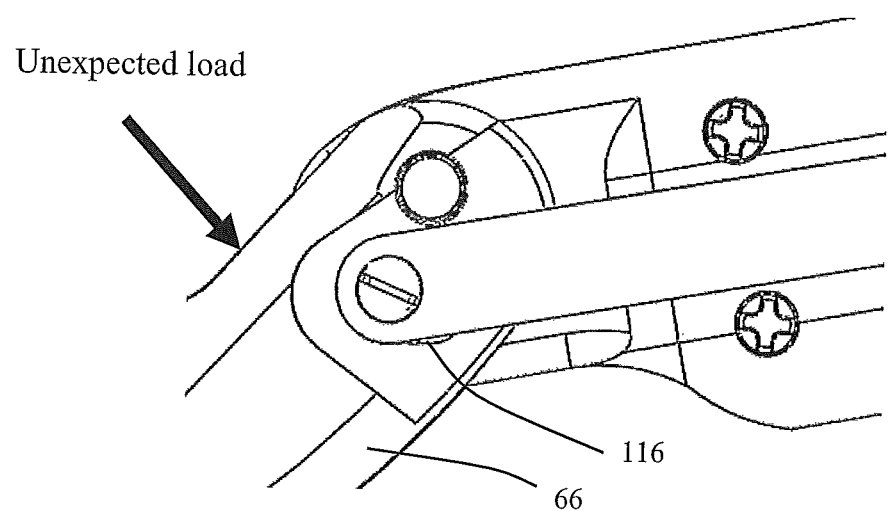
FIG. 16b shows a partial view of the proximal element, rod and distal element in the fully open position, the distal element having an alternative slot design and the distal element being pushed closed.

FIG. 16*a* shows the fourth pivot with the distal element having an alternative embodiment—the distal element has a more elongated left distal element slot 116 and right distal element slot 118 (not shown). The left third pivot 62 and the right third pivot 82 (not shown) sit inside a more elongated left distal element slot 116 and the right distal element slot 118 (not shown). FIG. 16*b* shows the left distal element 66 and the right distal element 92 (not shown) receiving an unexpected load and being pushed downwards by the force. Since the left distal element slot 116 and right distal element slot 118 (not shown) are more elongated the left distal element 66 and the right distal element 92 (not shown) are able to be pushed downwards, this can be used as a feature to protect the mechanical finger from accidental external shock.

While certain specific relationships, materials and other parameters have been detailed in the above description of a preferred embodiment, those can be varied, where suitable, with similar results. Other applications and variations of the present invention will occur to those skilled in the art upon reading the present disclosure. Those variations are also intended to be included within the scope of this invention as defined in the appended claims.

APPENDIX

List of Parts

10—Frame
12—Knuckle
14—First pivot
16—Second pivot
18—Rod
21—Third pivot
22—Screw nut boss
24—Proximal element
26—Force generator
28—Battery
32—Control sensor
34—Processor
36—Fourth pivot
38—Distal element
42—Proximal element slot
44—Distal element pivot aperture
45—Distal element follower
46—Elastic or spring element
47—Distal element slot
48—Knuckle to frame mount
52—Left knuckle
54—Right knuckle
56—Left second pivot
58—First pivot
62—Left third pivot
64—Left proximal element
66—Left distal element
68—Left rod
72—Right proximal element
74—Screw
76—Screw nut
78—Left proximal element slot
82—Right third pivot
84—Right proximal element slot
86—Sensor
88—Right knuckle to proximal element pivot
92—Right distal element
94—Left fourth pivot
96—Right fourth pivot
98—Right rod
102—Right knuckle to rod pivot
104—Microprocessor
106—Bearing for screw knuckle end
108—Bearing for screw distal end
112—Assembly screws
114—Left rod to third pivot
116—Left distal element slot
118—Right distal element slot
120—Right rod to third pivot
122—Left distal element area
124—Right distal element area 126—Left fourt pivot boss
128—Right fourth pivot boss
132—Left fourth pivot aperture
134—Right fourth pivot aperture
136—Left third pivot aperture
137—Right third pivot aperture
138—Left second pivot boss
139—Right rod boss
142—Rod aperture bearing
144—Rod boss bearing
146—Left second pivot aperture
148—Right second pivot aperture
152—Left first pivot aperture
154—Right first pivot aperture
156—Left first pivot boss
158—Right first pivot boss
160—Elongated Hole
162—Cylindrical Hole
164—Proximal element cavity

What is claimed is:

1. A mechanical finger comprising:
a mechanical knuckle having a first pivot attached to the mechanical knuckle and a second pivot attached to the mechanical knuckle, the second pivot being separated by a first predetermined distance from the first pivot;
a proximal element having a first proximal element end pivotally coupled to the first pivot and the proximal element having a third pivot at a variable longitudinal distance from the first pivot, wherein the proximal element rotates with respect to the mechanical knuckle around the first pivot in response to a change in the variable distance between the first pivot and the third pivot;
a rod having a first rod end pivotally coupled to the second pivot and a second rod end pivotally coupled to the third pivot;
a force generator driving a screw causing a translatory motion of a threaded screw nut that is threaded onto the screw, the screw being coupled to the proximal element and the threaded screw nut being coupled to the third pivot to change the variable longitudinal distance between the first pivot and the third pivot in response to a command from a control sensor to the force generator rotating the screw; and
a distal element, the distal element being pivotally coupled to the proximal element at a fourth pivot, the distal element rotating with respect to the proximal element around the fourth pivot in response to a change in the variable distance between the third pivot and the first pivot, wherein the distal element further comprises a distal element slot, wherein the third pivot includes a pivot boss connected to the threaded screw nut, said pivot boss engaging the distal element slot.

2. The mechanical finger of claim 1 further comprising:
a frame, the frame being formed to receive and be attached to the residual limb of a patient,
the mechanical knuckle being coupled to the frame.

3. The mechanical finger of claim 1 further comprising:
an elastic or spring element extending in tension from the distal element to the proximal element to add to the grip force and help maintain a closed grip as the power to the force generator is interrupted.

4. The mechanical finger of claim 1 wherein the proximal element further comprises:
a proximal element cavity accommodating
the threaded screw nut, the force generator being coupled to drive the screw in response to a control signal; and
a sensor coupled to the force generator for measuring the variable longitudinal distance between the first pivot and the third pivot.

* * * * *